US012802226B2

(12) United States Patent
McManis et al.

(10) Patent No.: US 12,802,226 B2
(45) Date of Patent: Nov. 17, 2026

(54) MACHINE FOR DETECTING A FOCAL CORTICAL DYSPLASIA LESION IN A BRAIN MAGNETIC RESONANCE IMAGING (MRI) IMAGE

(71) Applicants: BioVentures, LLC, Little Rock, AR (US); Arkansas Children's Research Institute, Little Rock, AR (US)

(72) Inventors: Mark McManis, Little Rock, AR (US); Freedom Perkins, Little Rock, AR (US)

(73) Assignees: BioVentures, LLC, Little Rock, AR (US); Arkansas Children's Research Institute, Little Rock, AR (US)

( * ) Notice: Subject to any disclaimer, the term of this patent is extended or adjusted under 35 U.S.C. 154(b) by 298 days.

(21) Appl. No.: 18/692,545

(22) PCT Filed: Sep. 16, 2022

(86) PCT No.: PCT/US2022/043811
§ 371 (c)(1),
(2) Date: Mar. 15, 2024

(87) PCT Pub. No.: WO2023/044009
PCT Pub. Date: Mar. 23, 2023

(65) Prior Publication Data

US 2024/0386563 A1 Nov. 21, 2024

Related U.S. Application Data

(60) Provisional application No. 63/244,862, filed on Sep. 16, 2021.

(51) Int. Cl.
*G06T 7/00* (2017.01)
*A61B 5/00* (2006.01)
*A61B 5/055* (2006.01)

(52) U.S. Cl.
CPC .......... *G06T 7/0014* (2013.01); *A61B 5/0042* (2013.01); *A61B 5/055* (2013.01);
(Continued)

(58) Field of Classification Search
CPC ......... G06T 7/0014; G06T 2207/10088; G06T 2207/30016; A61B 5/0042; A61B 5/055;
(Continued)

(56) References Cited

U.S. PATENT DOCUMENTS

2015/0289779 A1* 10/2015 Fischl .................... A61B 5/055 600/410
2022/0222816 A1* 7/2022 Carnell .................. G06T 15/08

FOREIGN PATENT DOCUMENTS

WO WO-2020219915 A1 * 10/2020 ............ G06N 3/047

* cited by examiner

*Primary Examiner* — Han Hoang
(74) *Attorney, Agent, or Firm* — Richard Blakely Glasgow

(57) ABSTRACT

A machine for detecting a focal cortical dysplasia lesion in a brain magnetic resonance imaging (MRI) image is disclosed. The machine includes a convolutional neural network in communication with a processor. The neural network includes an outer encoding layer, at least one inner encoding layer, at least one inner decoding layer, and an outer decoding layer. A method for training a convolutional neural network to detect focal cortical dysplasia lesions in brain MRI images and a method for detecting a focal cortical dysplasia lesion in an image are also disclosed.

14 Claims, 7 Drawing Sheets

(52) U.S. Cl.
CPC ............ *A61B 5/742* (2013.01); *A61B 5/7475* (2013.01); *G06T 2207/10088* (2013.01); *G06T 2207/30016* (2013.01)

(58) Field of Classification Search
CPC ...... A61B 5/742; A61B 5/7475; G16H 50/20; G16H 30/40
See application file for complete search history.

MACHINE FOR DETECTING A FOCAL CORTICAL DYSPLASIA LESION IN A BRAIN MAGNETIC RESONANCE IMAGING (MRI) IMAGE

CROSS-REFERENCE TO RELATED APPLICATIONS

This application claims the benefit of U.S. Provisional Application No. 63/244,862, entitled "Machine Learning Cortical Dysplasia Lesion Detection Software" and filed on Sep. 16, 2021. The complete disclosure of said provisional application is hereby incorporated by reference.

STATEMENT REGARDING FEDERALLY SPONSORED RESEARCH OR DEVELOPMENT

Not applicable

BACKGROUND

Cortical dysplasia is a congenital migrational disorder of brain development with a prevalence between 5% and 25% among patients diagnosed with epilepsy. When cortical dysplasia causes epilepsy, the seizures are often refractory to antiepileptic medications and surgery is often the best treatment option for these patients. Thus, the identification of cortical dysplasia can be an important factor in a patient's treatment plan. Identification of cortical dysplasia is typically done by radiologists looking through multiple MRI scans and sequences across multiple planes. The review can be time consuming even for experienced neuroradiologists and may sometimes still not detect cortical dysplasia.

Epilepsy affects 65M people worldwide with one-third of those people being drug resistant. That one-third accounts for 80% of the cost of $3-7B in healthcare & QOL. At forty percent (40%), Focal Cortical Dysplasia (FCD) is the leading cause of drug resistance. Fortunately, with surgery 80% of those individuals can be seizure-free. Unfortunately, FCD is difficult to detect and 50% of lesions are missed. Additionally, by 2025, the US will need 19% more neurologists to meet the need and demand. It would therefore be desirable to develop a machine learning cortical dysplasia lesion detection software to overcome these challenges.

The inventors have addressed this need for increased access to surgical treatment for drug-resistant epilepsy by developing artificial intelligence (AI)-based software to automatically review MRI data and identify FCD lesions. Many of the older papers describe using feature engineering to select features to reduce the computational burden. The inventors however are utilizing feature extraction which instead allows the system to determine what aspects of the information/data are relevant for discrimination. This is superior because it is using all the data and combining it for relevance and noise reduction. For more recent articles, while other researchers have promising models, almost without exception, they point to their lack of data as having hindered accuracy. Most had very small sample sizes (the average across 30 studies is n=38). Without enough examples, the algorithm cannot learn adequately in order to make a prediction accurately when faced with generalizing to new cases. The inventors will achieve their goal when the system's performance exceeds that of neuroradiologists. Past that, another standard is 90% or better and is based on the reality that, in a clinical setting, this is what clinicians seem to expect to have enough confidence to want to use a tool. While the goal would be to get as far above 90% as possible, the accuracy is dependent on the data. The inventors plan to continue to develop a large proprietary data set to be able to achieve this goal.

These and other features, objects and advantages of the present invention will become better understood from a consideration of the following detailed description of the preferred embodiments and appended claim in conjunction with the drawings as described following:

DISCLOSURE OF THE INVENTION

The present invention is directed to a machine for detecting a focal cortical dysplasia lesion in a brain magnetic resonance imaging (MRI) image, the machine comprising:

- at least one processor configured to execute instructions;
- at least one memory in communication with the processor, the memory being configured to store the instructions and be accessible by the processor to execute the instructions, wherein the instructions are operable to process the image;
- a convolutional neural network in communication with the processor, the neural network comprising:
  - an outer encoding layer configured to receive the image and apply an outer digital filter to the image to produce an outer filtered image map with large-scale features;
  - at least one inner encoding layer to receive both the image via a skip connection and the outer filtered image and apply an inner digital filter distinct from the outer digital filter to the outer filtered image to produce an inner filtered image map with small scale features, while retaining a set of original image features from the image;
  - at least one inner decoding layer to receive the inner filtered image map and apply an inner inverse convolution to the inner filtered image map to produce an inner decoded image map comprising a set of inner image features extracted from the image by the inner encoding layer; and
  - an outer decoding layer to receive the inner decoded image map and apply an outer inverse convolution to the inner decoded image map to produce an outer decoded image map comprising a set of outer image features extracted from the image by the outer encoding layer; and a user interface, wherein the instructions, when executed at the processor, are further operable to display the set of outer image features at the user interface.

The present invention is also directed to a method for training a convolutional neural network to detect focal cortical dysplasia lesions in brain magnetic resonance imaging (MRI) images, the method comprising the steps of:

- receiving a plurality of focal cortical dysplasia lesion MRI images, together with a plurality of image masks for each of the plurality of images, wherein each image mask comprises an indicator of an area of the corresponding image indicative of focal cortical dysplasia;
- converting the plurality of images into a plurality of image arrays, and converting the plurality of image masks into a plurality of image mask arrays;
- at a first resblock, encoding the plurality of image arrays and plurality of image mask arrays to produce a first encoded result; and
- at a second resblock, encoding the plurality of image arrays, plurality of image mask arrays, and the first encoded result to produce the second encoded result.

In addition, the present invention is directed to a method for detecting a focal cortical dysplasia lesion in an image, the method comprising the steps of:

at a first encoding layer of a convolutional neural network, applying a first digital filter to the image to produce a large-scale filtered image map;

at a second encoding layer of the convolutional neural network, applying a small-scale filter to both the image and the large-scale filtered image map to produce a small-scale filtered image map with small scale features that retains a set of original image features from the image;

at a first decoding layer, applying a first inverse convolution to the small-scale filtered image map to produce a first decoded image map comprising small-scale image features extracted from the image by the second encoding layer;

at a second decoding layer, applying a second inverse convolution to the first decoded image map to produce a second decoded image map comprising a second set of image features extracted from the image by the first encoding layer; and at a user interface, displaying the second decoded image map.

As described above, the present invention includes a proprietary software application that uses a deep learning algorithm to build a machine learning model to detect focal cortical dysplasia in MRIs of patients with seizures. The AI architecture is adapted from a fully convolutional neural network encoder-decoder architecture that has shown good performance in the field of medical imaging segmentation. The inventor's unique modification uses ResBlock encoders to preserve fine details through all of the encoding layers, improving overall performance in the identification of focal cortical dysplasia. This results in a report that clearly indicates to the reviewing physician the probability that there is focal cortical dysplasia present and where in the brain it is located.

The software application converts an MRI sequence into a three-dimensional array containing the values of each voxel. The three-dimensional array is then converted into a series of two-dimensional arrays with each two-dimensional array forming a slice. The core functionality of our system is the application of a formula, developed using machine learning, that computes a probability that the value of a voxel represents cortical dysplasia. The formula is applied to each voxel, in each slice, to generate a probability map of the presence of cortical dysplasia in the original MRI. The probability map is then used to generate an overlay for the original MRI that highlights regions where there is a high probability of a focal cortical dysplastic lesion for further review by the health care provider.

The present innovative machine learning approach overcomes several issues identified in the research literature surrounding the use of current machine learning models of surface feature variables. Two areas, in particular, are ResBlock encoders for detail preservation and layered encoders and decoders for image extraction. The present machine learning model instead uses a layered system of encoders and decoders to extract image features. Each encoding layer passes the encoded result to the subsequent layer, creating more detailed levels of analysis of the MRI. This can be done through as many layers as needed to encode sufficient details for feature identification. This novel system can evaluate the brain on both a slice-by-slice and voxel-by-voxel basis simultaneously from the MRI sequence to determine the chances of whether a lesion is present and, if so, where in the anatomical structure of the cortex it lies.

The generation of the formula to create the probability map was accomplished using a machine learning model that uses a layered series of convolutional neural networks (CNN) to analyze each MRI slice from a specially curated training dataset and encodes the features identified in the training data image that are most likely to signify the presence of focal cortical dysplasia in a brain MRI. Each CNN layer is a set of digital filters applied to the two-dimensional image. It is combined with dimension reduction and increased depth (pooling), and nonlinear activation function (ReLU) to generate a feature map. Each successive layer applies a different set of digital filters to the residual image data from the previous layer. That is, Layer 1 applies a set of digital filters to the MRI image and extracts the large-scale features from the image, resulting in a filtered secondary image. Layer 2 takes the filtered image from Layer 1 and applies a different set of digital filters to extract smaller-scale features, and the process is repeated for a total of five encoding layers.

The decoding phase of the machine learning algorithm starts with the feature map from the deepest layer (Layer 5) of encoding. The decoding uses the previously extracted features that are associated with focal cortical dysplastic brain lesions and applies an inverse convolution using the feature map extracted from the corresponding encoding layer. This process is the reverse of the digital filtering during encoding that emphasizes the features extracted during encoding to highlight potential regions with lesions while preserving the original image detail as the decoding progresses to the final layer and all of the original MRI data is incorporated into the final processed image. There is a decoding layer associated with each encoding layer and only the features from each encoding layer that are associated with identified lesions are added back to the image, thereby producing an image of the lesions.

The AI model computes a probability score that any given pixel represents focal cortical dysplasia, but it requires additional programming to decide what the threshold should be to display a pixel as Focal Cortical Dysplasia (FCD). The inventors also address pre- and post-processing. To improve the model during preprocessing, the inventors include balancing brightness and contrast and an AI filter to reduce noise in the images. The invention also displays the results in 3D to show the FCD lesion in relation to the whole brain.

The present invention was used in a pilot study in which an early version of the model was trained using preoperative axial FLAIR MRI images from 18 pediatric patients (aged 2 to 19 years) evaluated at an Epilepsy Monitoring Unit. These images were annotated based on radiological reports, post-surgical MRI, and pathology reports. After training, the model was tested with MRI images from a 10-year-old male patient with right temporal lobe dysplasia in whom cortical dysplasia was confirmed by post-surgical pathology review. The MRI slices from this patient and the corresponding masks generated by the present machine learning model were compared, indicating the dysplastic region. The results provide an early demonstration of the feasibility of using the present machine learning approach to detect FCD.

The current standard in the field is manual review. The innovation of the present invention lies in the application of a proprietary machine learning model, trained using a unique, diverse, and comprehensive proprietary dataset of annotated MRI images, as the basis of a novel software solution for processing MRI images and detecting FCDs. Although FCD is definitively diagnosed through histopathological identification of distinct cellular features of the brain tissue, there are distinct characteristics of FCD that can be seen in an MRI, including increased cortical FLAIR signal, blurring of the gray-white matter junction, increased cortical thickness, and other discreet signs. Currently, identification of these MRI features is based on a conventional visual inspection of the image sequences and is highly dependent on the training and experience of the interpreting physician. As noted above, FCD lesions are often heterogenous and atypical in their presentation, making them difficult to observe in the MRI, even for experienced physicians. Automated analysis of images using machine learning models offers a means of maximizing the sensitivity and specificity of lesion detection and removing the influence of variation in neuroradiologists experience, ensuring that all patients have access to the best standards of neuroradiology image analysis and lesion detection. Additional advantages include: (a) the software is designed to work with a range of image formats and imaging systems to ensure that it can be easily implemented regardless of a hospital's or imaging center's current MRI systems, (b) the software is adaptive, so that the more data it is given, the more it learns and the algorithm becomes more sensitive to detection of FCD, and (c) the software can be updated remotely to reflect the most up-to-date, accurate algorithms for processing MRIs to detect FCD. Use of the present invention in the field of medical neuroimaging provides the ability to detect abnormalities in the brain more accurately, specifically lesions that cause medication-resistant seizures, thereby increasing access to brain surgery.

The present invention increases access to surgical treatment for drug-resistant epilepsy by providing artificial intelligence (AI)-based software to automatically review MRI data and identify FCD lesions. This software, built on a machine learning model, fulfills the need for a rapid, sensitive screening method that can alleviate the burden of lesion identification on neuroradiologists, increase the speed of assessment, accurately identify the location of lesions, increase the rate of successful lesion identification, assess a patient's suitability for neurosurgery, and expand access to surgical treatment in hospitals where geographical, financial, and workload constraints exist. The software removes the need for a patient's initial MRI assessment to be performed at a specialized neurosurgical center, where expertise has traditionally been focused; instead, the software can be operated by any physician. Further, hospitals have financial incentives to adopt the use of the software, as neurosurgery often provides a critical income stream.

DETAILED DESCRIPTION OF THE INVENTION

Figure 1A:
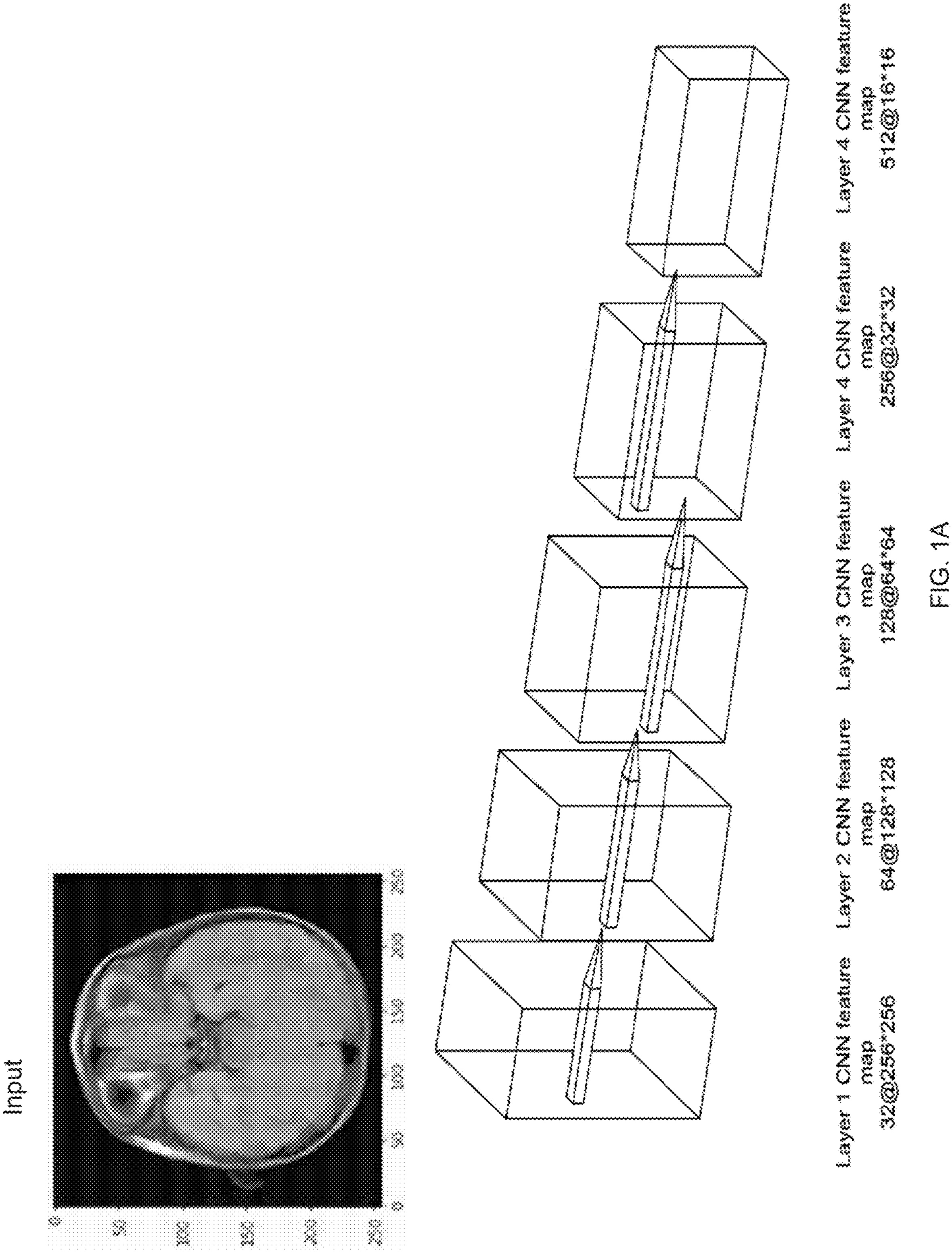
FIG. 1A is a diagram showing the sequence of convolutional neural networks for identifying MRI features that are associated with focal cortical dysplasia.
Figure 1B:
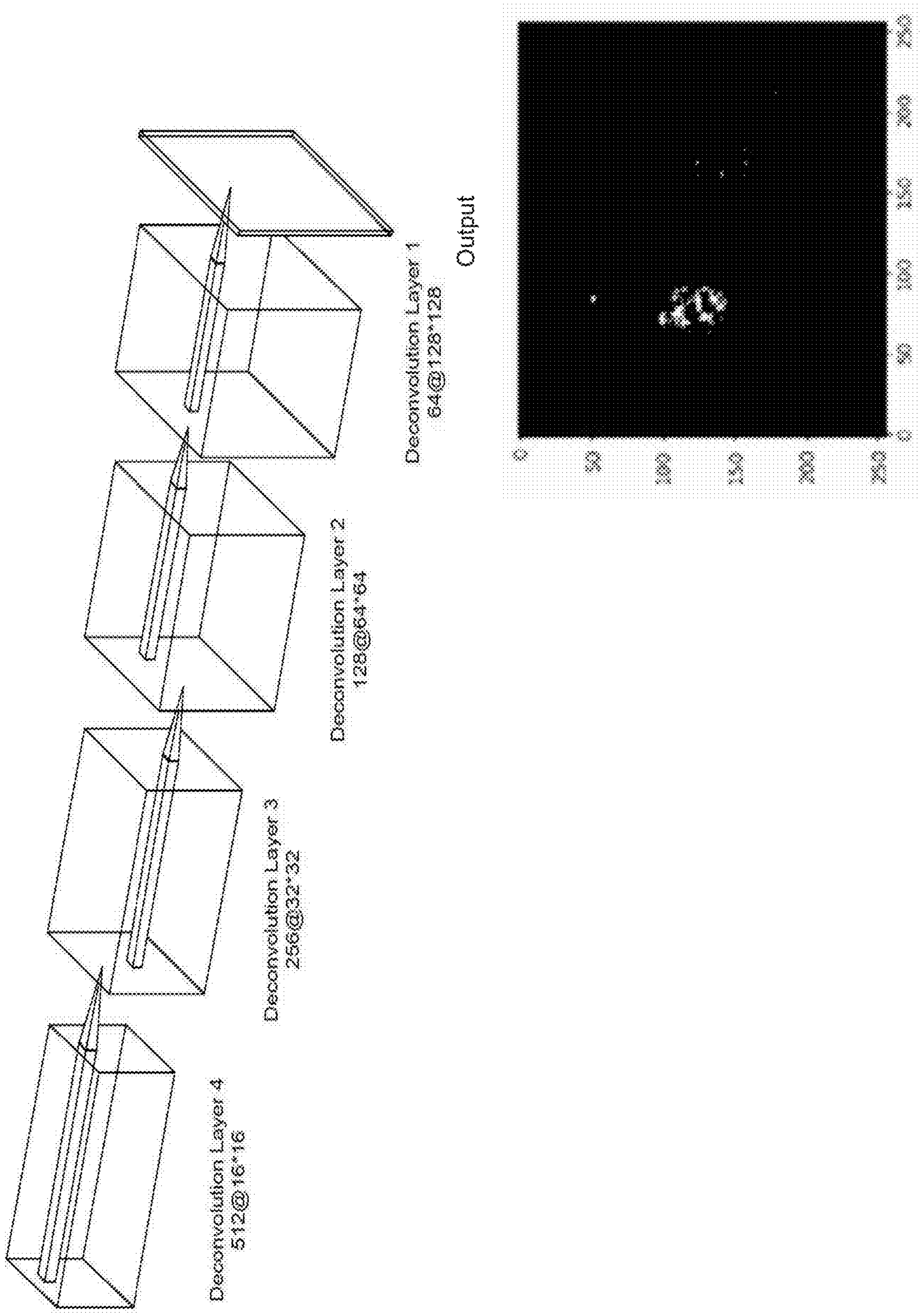
FIG. 1B is a diagram showing the sequence of deconvolutional neural networks to highlight features that are associated with focal cortical dysplasia in the MRI.

With reference to FIGS. 1A-6, the preferred embodiment of the present invention may be described. The present invention is directed to a machine learning cortical dysplasia lesion detection software.

The adaptive machine learning model is trained using a unique, diverse, and comprehensive proprietary data repository of annotated MRI images and is the basis of a novel software solution for processing MRI images and detecting Focal Cortical Dysplasias (FCDs). The inventors created the training dataset by reviewing fluid-attenuated inversion recovery (FLAIR) and/or T1-weighted MRI images from patients who have been diagnosed with FCD either from their imaging or pathology results. Each slice of the MRI sequence is reviewed for the presence of FCD and any part of the brain with FCD is annotated manually with 3D Slicer to create a "mask" of the lesion that is stored as a separate image sequence in the data repository. The image data from each DICOM MRI slice that comes from 3D Slicer (free, open-source software https://www.slicer.org/) and the corresponding mask slice is extracted and saved as NumPy arrays. NumPy arrays provide the flexibility to further process the MRI data using Python or Matlab. The arrays containing the image and mask data are saved as Python files in the data repository, making them available for additional processing and analysis.

The machine learning model uses a layered system of encoders and decoders to extract image features. Each encoder block is a ResBlock: two sequential convolutional neural networks (CNN) with non-linear activation between the CNNs and the original input is combined with the output of the second CNN. This preserves the fine details of the original image as it goes through successive levels of feature detection analysis. Each encoding layer passes the encoded result to the subsequent layer, creating more detailed levels of analysis of the MRI. This can be done through as many layers as needed to encode sufficient details for feature identification. This novel system can evaluate the brain on both a slice-by-slice and voxel-by-voxel (3-dimensional pixel) basis simultaneously from the MRI sequence to determine the chances of whether a lesion is present and, if so, where in the anatomical structure of the cortex it lies.

In addition to the fundamental architecture of the AI model, there are a number of hyperparameters that must be specified, and these have the effect of optimizing the model during training in order to generate the highest degree of sensitivity and specificity. Hyperparameter tuning involves selecting a method for measuring the rate of change, determining how large a change can be made to the model in a single iteration, and several other mathematical limitations on how the model can be adjusted in a single iteration. In many cases, these parameters are not wholly independent of one another and therefore the optimization is often accomplished by multiple training runs, adjusting the hyperparameters, and comparing the model accuracy. Thus, the hyperparameter optimization is often done on a relatively small subset of the full dataset in order to speed up the optimization process. The neural network used in the present invention combines several techniques, which is not accidental for a challenging problem. It is a variation of an encoder-decoder architecture, which is well-known for its very good performance in a variety of medical segmentation tasks (e.g., Ronneberger et al., 2015). However, the Res Block encoder is used to preserve the fine detail in the deeper levels of the feature encoding layers.

The model emerged from an experimental stage. During prototyping, the inventors leveraged many other techniques and applied them to a general encoder-decoder structure. ResBlock is the main element of the architecture the inventors are now using. It contains two convolutions, ReLU activation functions, and batch normalization with the same number of groups as channels. This is followed by skip connection at the end of the block. The encoder has three levels. Except for the first level, where additional ResBlock is used, each level has two ResBlocks, with the first one increasing the number of channels by two. Strided convolutions are used as downsampling layers. There are also BatchNormalization layers, which normalize the input with zero-mean. The decoder uses only single ResBlock for each level. After upsampling with simple trilinear interpolation, the output is concatenated with the skip from the corresponding level of the encoder. At the end, sigmoid activation function was applied to make sure that every value of probability map of segmentation was in the 0-1 range.

In short, the AI model "learns" by building a complex mathematical formula (model) of a dataset (training data) with a known solution (FCD vs. not FCD). The output of the model is then compared to a separate dataset (test data) that has a known solution and the computer makes iterative adjustments to the model to improve its performance against the test data. The rate or magnitude of the changes made to the model are referred to as the gradient. The model goes through multiple iterations, each time making adjustments, and is considered fully trained when the rate of change approaches zero. The hyperparameters guide how the model makes adjustments and can affect the ultimate state of the final model solution, where the sensitivity and specificity of lesion detection is determined as measures of accuracy. The software may be housed on a stand-alone laptop with a user-friendly interface and report generator, both proprietary. The software is designed to work with a range of image formats and imaging systems to ensure that it can be easily implemented regardless of a hospital's current MRI systems. A user interface will allow users to import images directly from their PACS system into the analysis software or import from a DICOM file on CD/DVD/disk. The inventors also plan to include the ability to remotely update the software as more data become available and the algorithm becomes more sensitive.

The invention includes additional features beyond the AI model. These features enhance the algorithm, which is made up of three parts. The first part is preprocessing applied to the images, the second is the segmentation process where every voxel is assigned a probability of representing FCD, and the final step in the algorithm is determining what threshold of probability is used to present an image as FCD to the end user. To improve the model during preprocessing, the inventors include balancing brightness and contrast and an AI filter to reduce noise in the images. The AI model computes a probability score that any given pixel represents focal cortical dysplasia, but it requires additional programming to decide what the threshold should be to display a pixel as FCD. The results may be displayed in 3D to show the FCD lesion in relation to the whole brain.

Figure 6:
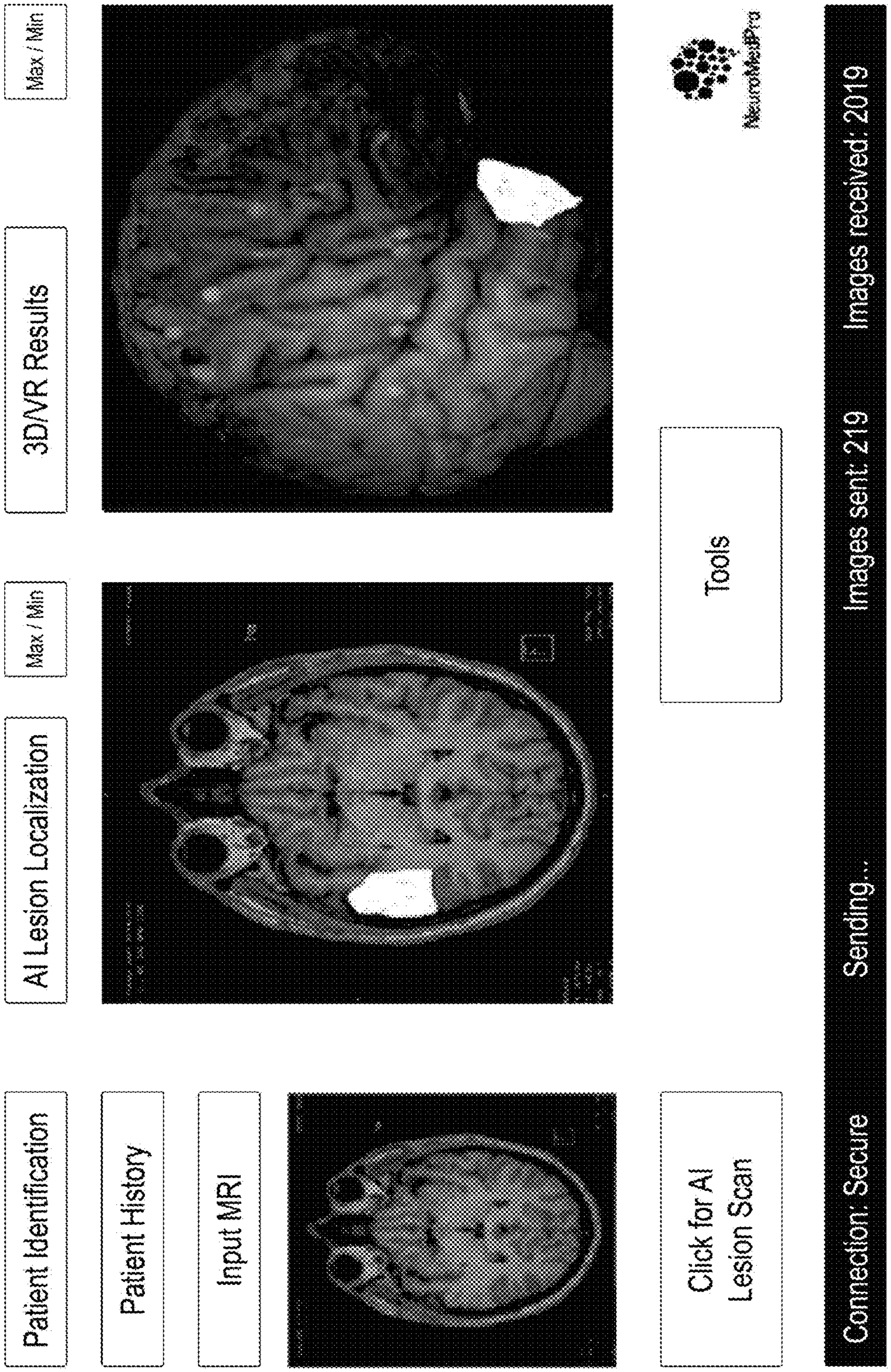
FIG. 6 is a diagram of the user interface of the present invention.

The present system wraps an intuitive clinical interface around a unique machine learning algorithm running on a HIPAA-compliant cloud server to segment a brain MRI sequence and highlight lesions identified in the MRI for further clinical evaluation. The resulting MRI sequence is then combined and presented as a 3D/Virtual Reality model for visualization of the identified lesions. The user interface is shown in FIG. 6.

The user interface is intuitive for clinical users with a clear area on the left-hand side of the screen for putting in the patient identifier and relevant patient history to aid in the evaluation of the patient's MRI. There is a button to add the patient MRI and a graphical window on the left side of the screen to show the user that the MRI has been loaded. There is a large button that transmits the MRI to the cloud server for evaluation by the AI model. The bottom of the interface shows the status of the secure transmission of the image sequences, allowing the user to monitor the transmission. There are two windows for results returned from the cloud server after processing by the AI model. In the central window labeled "AI Lesion Localization" the interface displays the processed MRI with potential areas of focal cortical dysplasia highlighted in white, for further review. The mouse wheel allows the user to scroll through the entire MRI sequence. In addition to the highlighted MRI sequence, a secondary visualization appears on the right side of the screen to show the user a 3D reconstruction of the MRI with any potential lesional area highlighted. This 3D reconstruction can be rotated in any direction for review. Buttons above each of the output windows allow the user to toggle between full-screen view and window view for the output. In addition, there is a button that pulls up a list of tools for the user for measuring angles and distances in the MRI and adding notations to individual MRI slices for clinical notes.

Figure 5:
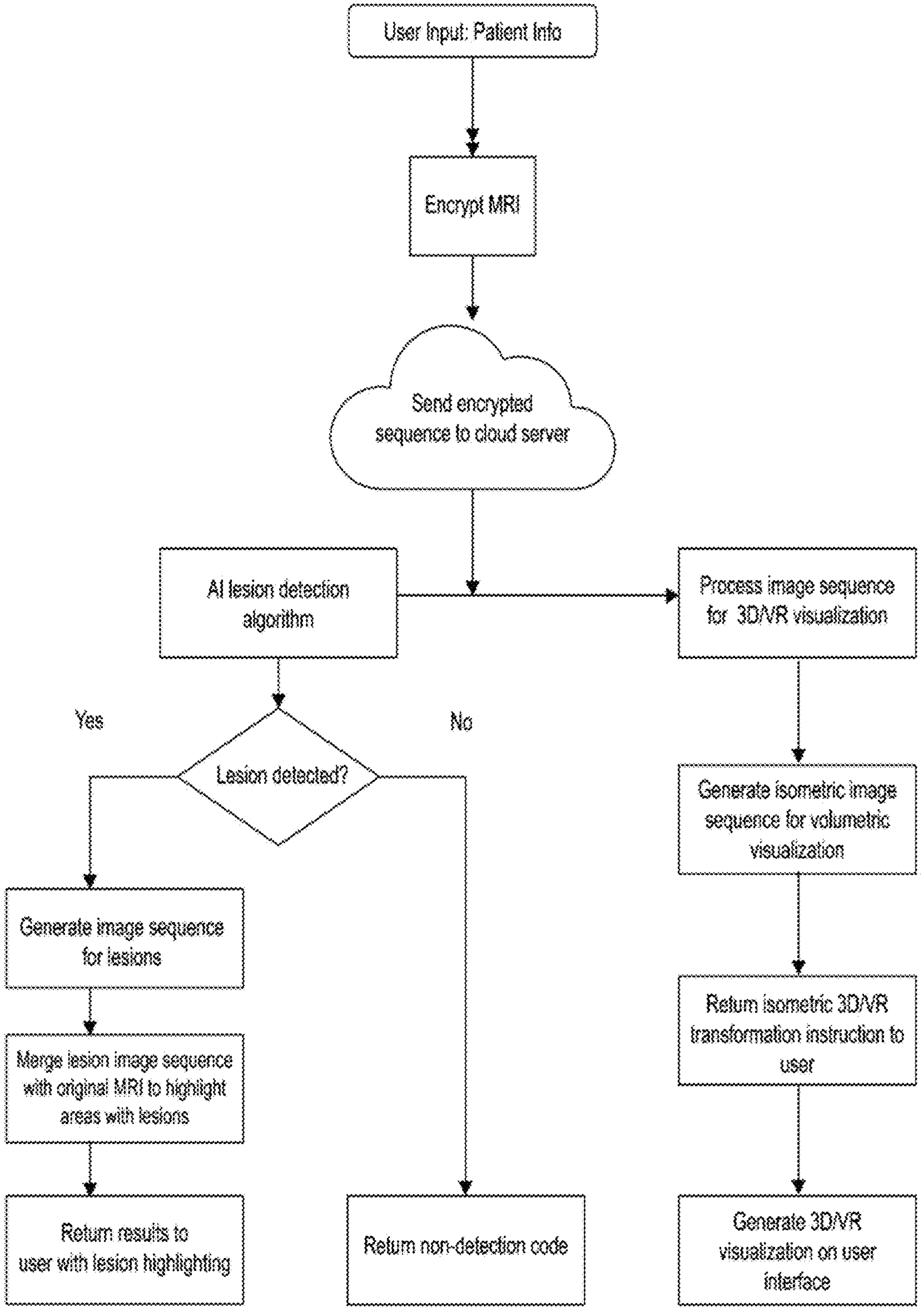
FIG. 5 is a flow chart showing the steps of the present invention for detecting lesions.

A flow chart showing the steps for detecting lesions is shown in FIG. 5. The operational flow of the system starts with the user entering the necessary patient information into the user interface, including the Patient ID and the MRI sequence. The MRI is then encrypted at the user's site before the MRI is transmitted to a HIPAA-compliant cloud server for processing. Once received at the server, the MRI is decrypted, but the patient identifiable data is separated from the image data and kept encrypted. The MRI sequence is converted into a three-dimensional array containing the values of each voxel. The three-dimensional array is then converted into a series of two-dimensional arrays with each two-dimensional array forming a slice. The image data is then processed through the AI model. The first stage is preprocessing the images to balance brightness and contrast. The values for Window and Level are set to the default and the image data is normalized across all images in the sequence to ensure all values for the voxels are between 0 and 1. The normalization process is a linear transformation that adds a constant value to all voxel values to make all values positive. Then the mean and standard deviation are computed and all values greater than three standard deviations above the mean are set to be three standard deviations above the mean. Finally, all the voxels are divided by the maximum value of the 3D array to set all values between 0 and 1, in order to be processed through the AI model for lesion detection.

The AI model is a computer engine that has been trained to recognize specific patterns in the values within the array of voxels and assign a probability that the pattern seen in the array of voxels signifies the presence of focal cortical dysplasia in the patient's MRI. The engine processes each voxel of the 3D image data array and generates a 3D array, of the same size and shape as the image array, which stores the likelihood (probability) that the corresponding voxel in the image data array represents focal cortical dysplasia, as determined by the AI model. This "probability map" array is further processed by setting all values below the threshold to zero and all values above the threshold to one. Then the entire probability map is processed through a nearest-neighbor clustering algorithm to eliminate any singular voxels that may have been assigned a high probability score but do cover a large enough volume to warrant further clinical review. Finally, the image data array locations corresponding to the X, Y, and Z coordinates of the probability map array with values equal to one are highlighted and are returned for review with the highlighted voxels in each slice clearly visible to the user.

Additional processing of the image data is done to prepare the MRI image for 3D visualization. This processing uses a boundary algorithm to remove the outer edges of each slice of the image, representing skin, bone, and cerebrospinal fluid, leaving just the cortical and subcortical structures in the image. Further processing stacks the image sequence in the proper order and applies a spatial normalization, based on the data from the original MRI to generate the 3D visualization.

PILOT PROJECT: Methods: For this pilot project, the preoperative axial FLAIR MRIs from 18 pediatric patients who were evaluated at the EMU at Dell Children's Medical Center in Austin, TX, were used. Patients ranged from 2 to 19 years of age. The MRIs were acquired on a 1.5T Siemens magnet during the surgical evaluation for each patient and the axial FLAIR sequence was selected as a common sequence across all patients. Slices in the axial FLAIR sequence were 5 mm thick and spacing was 6.25 mm.

In order for the ML system to correctly segment and label an image, the ML model must be trained on a set of images that have been annotated to indicate to the computer model what regions of the image show dysplasia. The images for this pilot study were annotated based on the radiological report, postsurgical MRI images, and pathology reports for each patient. To increase the number of images used for training, each MRI slice was rotated 90, 180, and 270 degrees. There were 1632 axial FLAIR images used to train the model. Each image was centered in a 256 by 256 voxel array.

The ML model was built in Python 3.6 using the Tensorflow platform. The architecture was a U-Net convolutional neural network. The U-Net architecture involves a contraction path to extract advanced features in the image, but also reduces the size of feature maps. Thus, an expansion path is needed to recover the size of the feature map (see FIGS. 1A-1B). Finally, a concatenation path is used to combine the contraction and expansion feature maps to generate a complete feature map for segmentation and labeling of the image.

Figure 2:
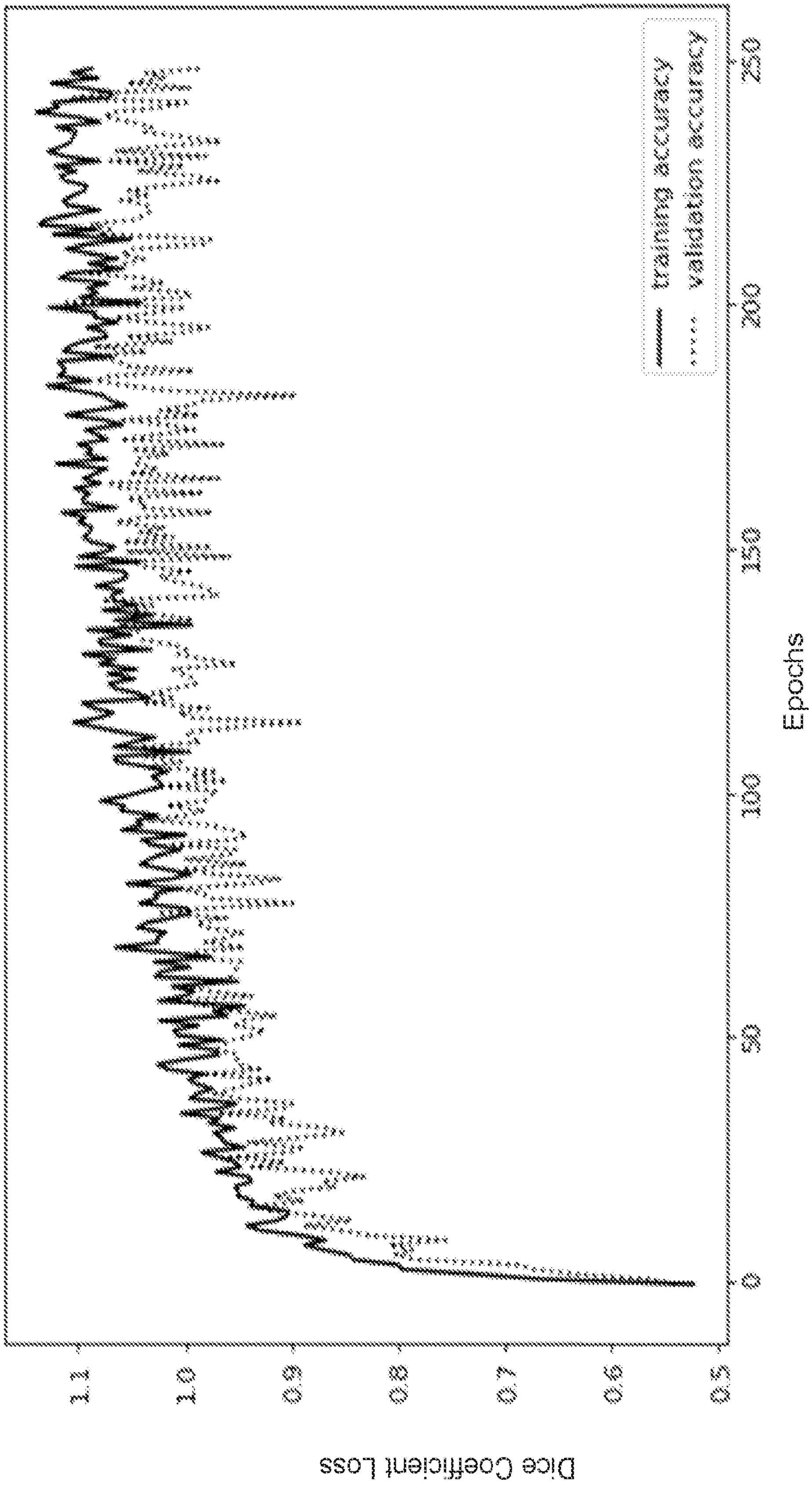
FIG. 2 is a graph showing the accuracy of model classification for training and validation data sets measured using the Modified Dice Coefficient method.
Figure 3:
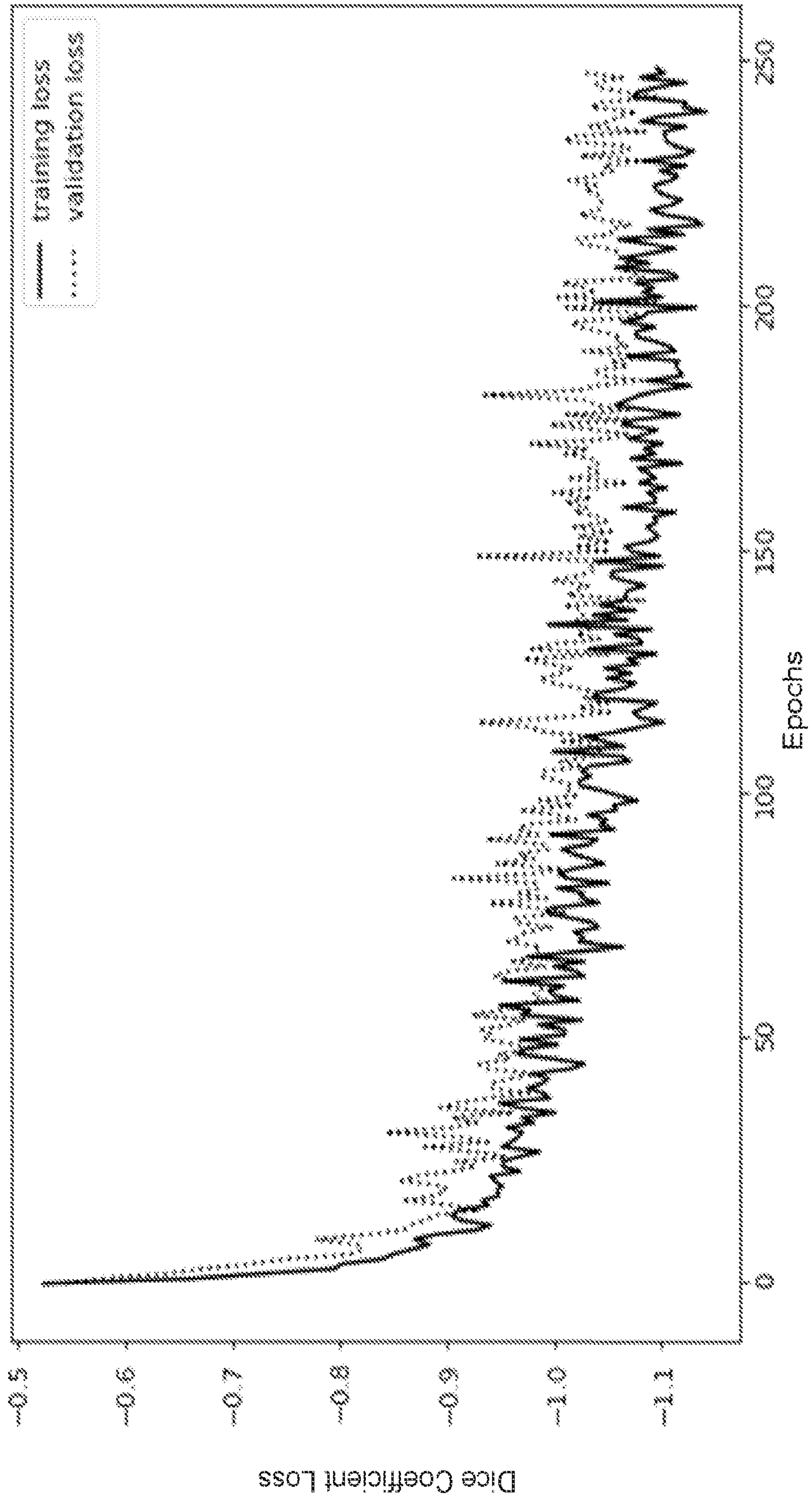
FIG. 3 is a graph showing the loss function of model classification accuracy for training and validation data sets measured using the Modified Dice Coefficient Loss method.
Figure 4:
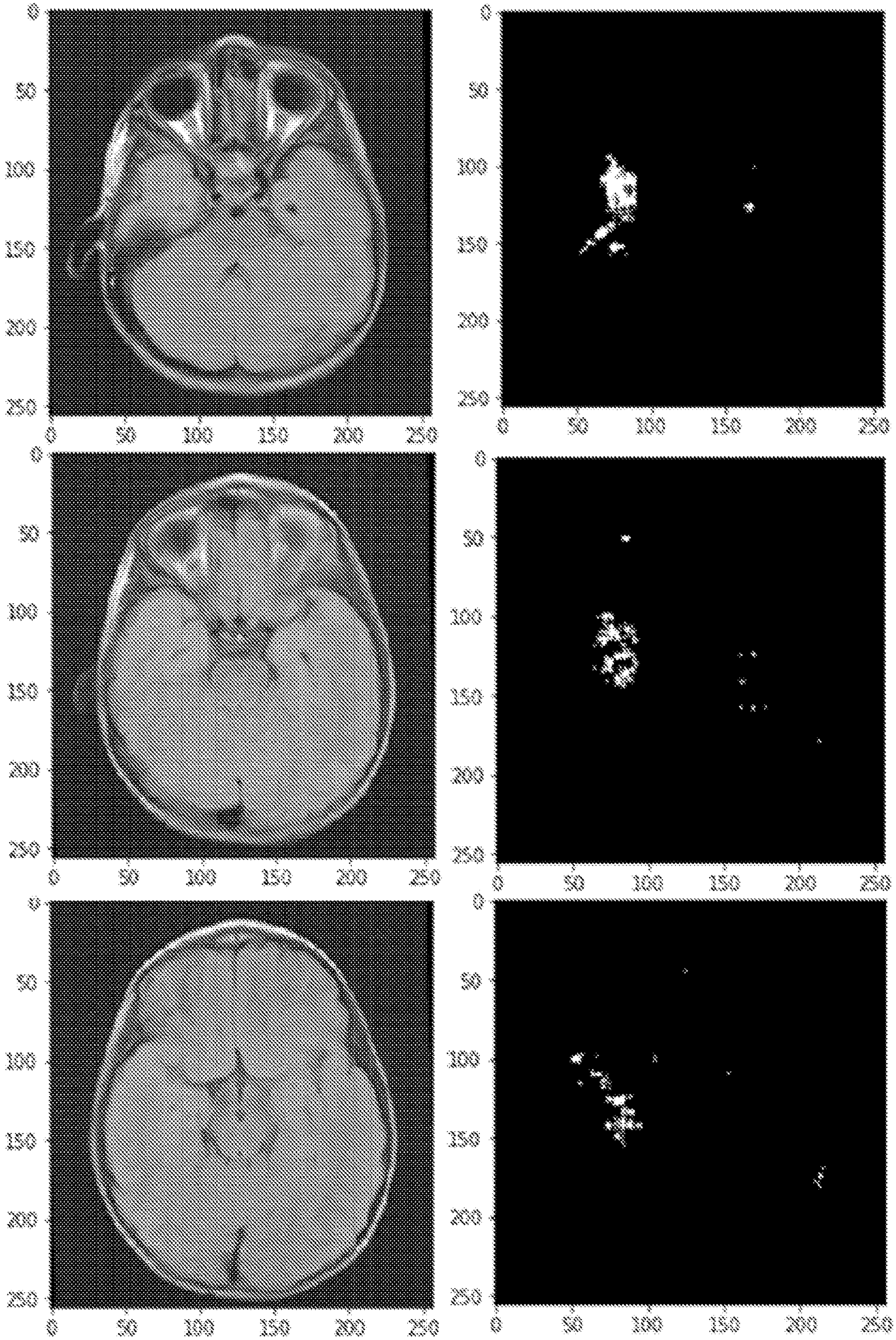
FIG. 4 shows MRI slices (left-top, left-middle, and left-bottom) and the dysplastic region mask generated by the trained network (right-top, right-middle, and right-bottom).

Results: The model was trained for 250 epochs. FIGS. 2 and 3 show the training accuracy and loss, respectively. After training, the model was tested with a patient with right temporal lobe dysplasia. FIG. 4 shows the MRI slice (left side of figure) and the corresponding mask of the dysplastic region generated by the trained network (right side of figure). The cluster of white pixels in the right-hand column corresponds to the dysplastic region in the images to the left. The patient is a 10-year-old male with a history of refractory epilepsy, autism spectrum disorder associated with Mowat-Wilson syndrome and focal cortical dysplasia. His epilepsy has been refractory to multiple medications as well as focal laser thermal ablation to his right parietal lobe and anterior superior insula. A biopsy of the parietal lesion showed focal cortical dysplasia type 1A. MR imaging demonstrates post-surgical changes of the right anterosuperior frontal and right parietal lobes. There are multifocal subependymal heterotopia as well as indistinct gray-white matter differentiation of the right anterior temporal lobe. On imaging there is also a suggestion of evolving right mesial temporal sclerosis. See FIG. 4.

Conclusions: This pilot study demonstrates the feasibility of using machine learning to aid in the interpretation of brain MRIs. Even with only a small number of patients, the network was able to identify regions of cortical dysplasia in a patient. This project is limited by the number of patients and the use of only FLAIR images.

Future Development: The inventors are conducting research to further develop and confirm the accuracy of the model in three main stages: (1) develop a large expert-annotated MRI dataset for focal cortical dysplasia, (2) increase the accuracy of focal cortical lesion detection with an enhanced ML algorithm, and (3) prospectively test the output of the trained ML model against radiological and post-surgical pathology identification of focal cortical dysplasia.

The inventors are developing a commercial application of AI to detect focal cortical dysplasia lesions. The inventors are taking a "by clinicians for clinicians" approach to the software development program, ensuring that the user interface and features of the software are tailored toward clinicians' needs. The inventors believe the growing acceptance of the role of AI in radiology, their focus on the key clinical problem of lesion identification in epilepsy, and the benefits for patients and clinicians will overcome the main barriers to commercialization of their software and ensure a competitive advantage.

The present invention has been described with reference to certain preferred and alternative embodiments that are intended to be exemplary only and not limiting to the full scope of the present invention as set forth in the appended claims.

We claim:

1. A machine for detecting a focal cortical dysplasia lesion in a brain magnetic resonance imaging (MRI) image, the machine comprising:

at least one processor configured to execute instructions;

at least one memory in communication with the processor, the memory being configured to store the instructions and be accessible by the processor to execute the instructions, wherein the instructions are operable to process the image;

a convolutional neural network in communication with the processor, the neural network comprising:

an outer encoding layer configured to receive the image and apply an outer digital filter to the image to produce an outer filtered image map with large-scale features;

at least one inner encoding layer to receive both the image via a skip connection and the outer filtered image map and apply an inner digital filter distinct from the outer digital filter to the outer filtered image map to produce an inner filtered image map with small scale features, while retaining a set of original image features from the image, wherein each of the outer encoding layer and the at least one inner encoding layer comprises a residual block, the residual block comprising a first convolutional neural network, a non-linear activation function, and a second convolutional neural network arranged in sequence, and wherein an input to the residual block is combined with an output of the second convolutional neural network so as to preserve fine details of the image through each of the outer encoding layer and the at least one inner encoding layer;

at least one inner decoding layer to receive the inner filtered image map and apply an inner inverse convolution to the inner filtered image map to produce an inner decoded image map comprising a set of inner image features extracted from the image by the inner encoding layer; and an outer decoding layer to receive the inner decoded image map and apply an outer inverse convolution to the inner decoded image map to produce an outer decoded image map comprising a set of outer image features extracted from the image by the outer encoding layer; and a user interface, wherein the instructions, when executed at the processor, are further operable to compute, from the outer decoded image map, a probability that each of a plurality of voxels of the image represents focal cortical dysplasia, and to display at the user interface an overlay of the image highlighting each voxel for which the computed probability exceeds a threshold.

2. The machine of claim 1, wherein the instructions, when executed at the processor, are operable to sequence the image into a three-dimensional array comprising a plurality of voxels.

3. The machine of claim 2, wherein the instructions, when executed at the processor, are further operable to convert the three-dimensional array into a plurality of two-dimensional array slices.

4. The machine of claim 3, wherein the instructions, when executed at the processor, are further operable to process the three-dimensional array and the two-dimensional array slices simultaneously.

5. The machine of claim 1, wherein the instructions, when executed at the processor, are further operable to apply a boundary algorithm to each slice of the image to remove outer edges of the image slice comprising at least one of skin, bone, and cerebrospinal fluid, leaving cortical and subcortical structures in the slice, and to stack the resulting slices and apply a spatial normalization based on the image so as to generate a three-dimensional visualization for display at the user interface.

6. A method for detecting a focal cortical dysplasia lesion in an image, the method comprising the steps of:

at a first encoding layer of a convolutional neural network, applying a first digital filter to the image to produce a large-scale filtered image map;

at a second encoding layer of the convolutional neural network, applying a small-scale filter to both the image and the large-scale filtered image map to produce a small-scale filtered image map with small scale features that retains a set of original image features from the image, wherein each of the first encoding layer and the second encoding layer comprises a residual block, and wherein applying the digital filter at each of the first encoding layer and the second encoding layer comprises passing an input to the residual block through a first convolutional neural network, a non-linear activation function, and a second convolutional neural network in sequence, and combining the input to the residual block with an output of the second convolutional neural network;

at a first decoding layer, applying a first inverse convolution to the small-scale filtered image map to produce a first decoded image map comprising small-scale image features extracted from the image by the second encoding layer;

at a second decoding layer, applying a second inverse convolution to the first decoded image map to produce a second decoded image map comprising a second set of image features extracted from the image by the first encoding layer; and at a user interface, displaying the second decoded image map.

7. The method of claim 6, further comprising the step of converting the image into a voxel array comprising a plurality of voxels before the step of applying the first digital filter.

8. The method of claim 7, further comprising the step of converting the image into a slice array comprising a plurality of two-dimensional image slices before the step of applying the first digital filter.

9. The method of claim 8, further comprising the step of applying a threshold to the second decoded image map to produce an overlay.

10. The method of claim 6, further comprising the step of applying a boundary algorithm to each slice of the image so as to prepare a three-dimensional visualization of the image, wherein the step of applying the boundary algorithm comprises the step of removing any outer edges of the slice comprising at least one of skin, bone, and cerebrospinal fluid so as to leave cortical and subcortical structures in the slice, and further comprising the steps of stacking the slices in order and applying a spatial normalization based on the image so as to generate the three-dimensional visualization.

11. The machine of claim 1, wherein the instructions, when executed at the processor, are further operable to generate a probability map from the computed probabilities and to apply a nearest-neighbor clustering algorithm to the probability map so as to eliminate singular voxels for which the computed probability exceeds the threshold but which do not cover a volume sufficient to warrant clinical review.

12. The machine of claim 1, wherein the instructions, when executed at the processor, are further operable, prior to processing the image through the convolutional neural network, to normalize the image by adding a constant value to each voxel value so as to render each voxel value positive, by setting each voxel value greater than three standard deviations above a mean voxel value to three standard deviations above the mean voxel value, and by dividing each voxel value by a maximum voxel value, such that all voxel values fall between zero and one.

13. The machine of claim 1, wherein the convolutional neural network comprises at least three encoding layers and a corresponding decoding layer for each of the at least three encoding layers, and wherein each decoding layer receives, by concatenation, a skip output from the corresponding encoding layer.

14. The machine of claim 5, wherein the three-dimensional visualization is rotatable in any direction at the user interface.

* * * * *